(12) United States Patent
Matthison-Hansen

(10) Patent No.: US 10,779,710 B2
(45) Date of Patent: Sep. 22, 2020

(54) ENDOSCOPE

(71) Applicant: AMBU A/S, Ballerup (DK)

(72) Inventor: Kaspar Mat Matthison-Hansen, Helsingør (DK)

(73) Assignee: AMBU A/S, Ballerup (DK)

( * ) Notice: Subject to any disclaimer, the term of this patent is extended or adjusted under 35 U.S.C. 154(b) by 224 days.

(21) Appl. No.: 15/576,818

(22) PCT Filed: May 26, 2016

(86) PCT No.: PCT/DK2016/050148
§ 371 (c)(1),
(2) Date: Nov. 25, 2017

(87) PCT Pub. No.: WO2016/188537
PCT Pub. Date: Dec. 1, 2016

(65) Prior Publication Data
US 2018/0303317 A1   Oct. 25, 2018

(30) Foreign Application Priority Data
May 27, 2015 (DK) .................................. 2015 70323

(51) Int. Cl.
*A61B 1/00* (2006.01)
*A61B 1/005* (2006.01)
(Continued)

(52) U.S. Cl.
CPC .......... *A61B 1/0052* (2013.01); *A61B 1/0011* (2013.01); *A61B 1/0057* (2013.01);
(Continued)

(58) Field of Classification Search
None
See application file for complete search history.

(56) References Cited

U.S. PATENT DOCUMENTS

| 609,570 A | 8/1898 | Bowden |
| 4,203,430 A | 5/1980 | Takahashi |
| (Continued) | | |

FOREIGN PATENT DOCUMENTS

| AU | 2008207558 A1 | 4/2009 |
| CN | 1125390 | 6/1996 |
| (Continued) | | |

OTHER PUBLICATIONS

Danish Patent and Trademark Office Search Report for Appl No. PA201570323 dated Jul. 9, 2015, 8 pages.
(Continued)

*Primary Examiner* — Timothy J Neal
(74) *Attorney, Agent, or Firm* — Faegre Drinker Biddle & Reath LLP

(57) ABSTRACT

An endoscope having an operating handle comprising a handle housing arranged at a proximal end and an insertion tube extending from said handle towards a distal end of the endoscope and terminating in a steerable tip part at the distal end of the endoscope, the endoscope further comprising a control mechanism with a Bowden cable having an outer guide tube having a first length between a proximal end and a distal end of said outer guide tube and an inner pull-wire having a second length between a proximal end and a distal end of said inner pull-wire, said second length being longer than said first length, the proximal end of the outer guide tube is affixed to the operating handle by means of an adhesive.

20 Claims, 9 Drawing Sheets

Figure 1:
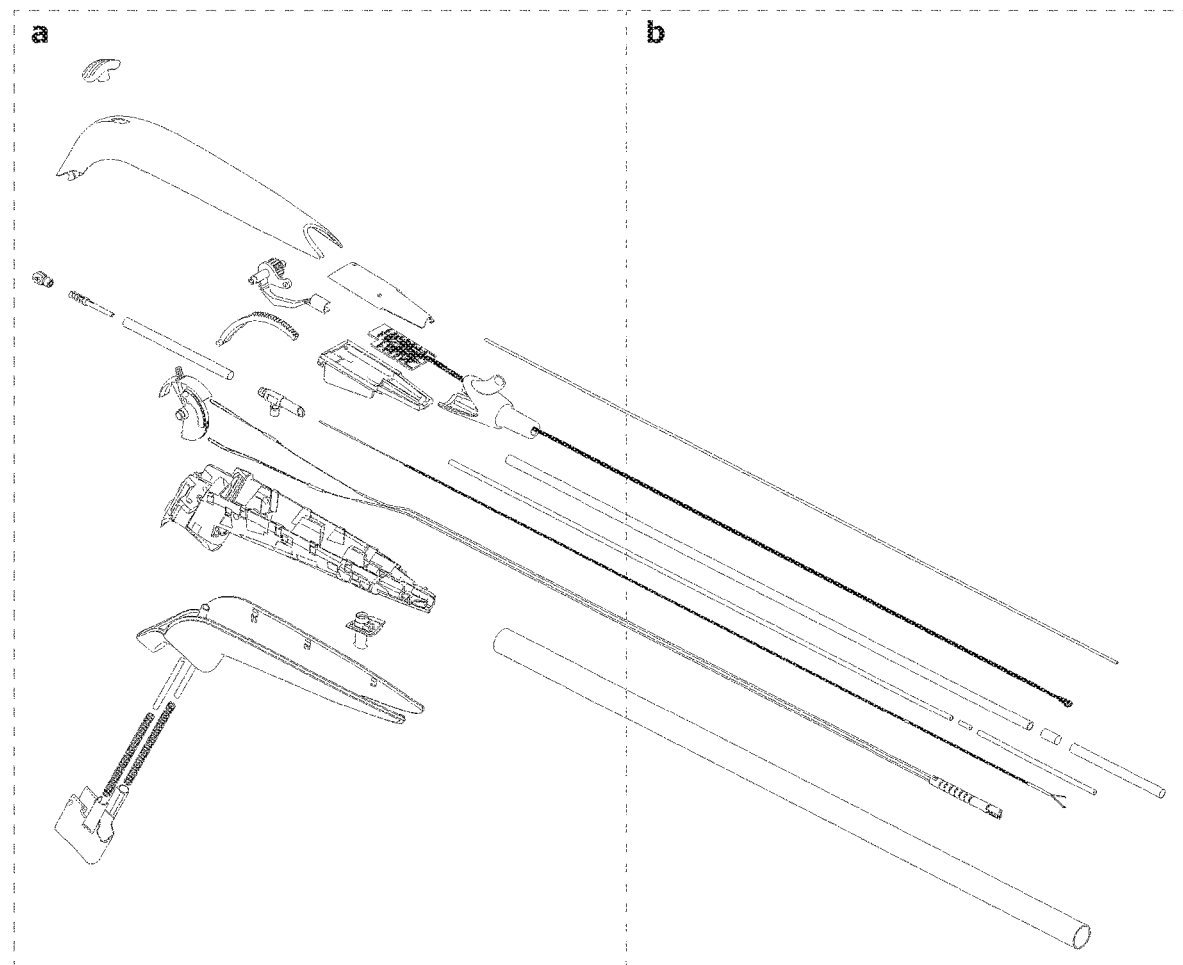

(51) Int. Cl.
- *H04N 5/225* (2006.01)
- *H04N 5/232* (2006.01)
- *A61B 1/018* (2006.01)
- *H04N 7/10* (2006.01)
- *A61M 25/01* (2006.01)

(52) U.S. Cl.
CPC ...... *A61B 1/00066* (2013.01); *A61B 1/00103* (2013.01); *A61B 1/018* (2013.01); *H04N 5/2251* (2013.01); *H04N 5/23293* (2013.01); *A61M 25/0136* (2013.01); *H04N 7/102* (2013.01); *H04N 2005/2255* (2013.01)

(56) References Cited

U.S. PATENT DOCUMENTS

| | | | |
|---|---|---|---|
| 4,750,475 | A | 6/1988 | Yoshihashi |
| 4,757,827 | A | 7/1988 | Buchbinder et al. |
| 4,805,596 | A | 2/1989 | Hatori |
| 4,905,666 | A * | 3/1990 | Fukuda .......... A61B 1/0052 600/146 |
| 5,167,221 | A | 1/1992 | Chikama |
| 5,275,151 | A | 1/1994 | Shockey et al. |
| 5,299,562 | A | 4/1994 | Heckele et al. |
| 5,373,317 | A | 12/1994 | Salvati et al. |
| 5,435,805 | A | 7/1995 | Bowden |
| 5,450,851 | A | 9/1995 | Hancock |
| 5,462,527 | A | 10/1995 | Stevens-Wright et al. |
| 5,810,876 | A | 9/1998 | Kelleher |
| 5,879,289 | A | 3/1999 | Yarush et al. |
| 5,938,588 | A * | 8/1999 | Grabover .......... A61B 1/0057 600/143 |
| 6,007,531 | A | 12/1999 | Snoke et al. |
| 6,077,277 | A | 6/2000 | Mollenauer et al. |
| 6,258,101 | B1 | 7/2001 | Blake et al. |
| 6,270,508 | B1 | 8/2001 | Klieman et al. |
| 6,390,972 | B1 | 5/2002 | Speier et al. |
| 8,790,250 | B2 | 7/2014 | Petersen |
| 10,617,284 | B2 | 4/2020 | Matthison-hansen |
| 10,624,531 | B2 | 4/2020 | Matthison-hansen |
| 10,624,617 | B2 | 4/2020 | Matthison-hansen et al. |
| 10,631,716 | B2 | 4/2020 | Matthison-hansen |
| 10,645,260 | B2 | 5/2020 | Matthison-hansen et al. |
| 10,646,107 | B2 | 5/2020 | Matthison-hansen et al. |
| 2002/0099266 | A1 | 7/2002 | Ogura et al. |
| 2003/0009176 | A1 | 1/2003 | Bilitz |
| 2005/0070764 | A1 | 3/2005 | Nobis et al. |
| 2005/0075539 | A1 | 4/2005 | Schulz et al. |
| 2005/0273085 | A1 | 12/2005 | Hinman et al. |
| 2006/0025651 | A1 | 2/2006 | Adler et al. |
| 2006/0173243 | A1 | 8/2006 | Watanabe |
| 2006/0258955 | A1 | 11/2006 | Hoffman et al. |
| 2007/0219411 | A1 | 9/2007 | Dejima et al. |
| 2007/0250038 | A1 | 10/2007 | Boulais |
| 2007/0282167 | A1 | 12/2007 | Barenboym et al. |
| 2008/0051631 | A1 | 2/2008 | Dejima et al. |
| 2008/0188868 | A1 | 8/2008 | Weitzner et al. |
| 2008/0195128 | A1 | 8/2008 | Orbay et al. |
| 2008/0249483 | A1 * | 10/2008 | Slenker .......... A61B 1/0055 604/275 |
| 2008/0287735 | A1 | 11/2008 | Takemoto et al. |
| 2009/0054733 | A1 | 2/2009 | Marescaux |
| 2009/0076328 | A1 | 3/2009 | Root et al. |
| 2009/0209945 | A1 * | 8/2009 | Lobl .......... A61M 5/14224 604/891.1 |
| 2009/0247994 | A1 | 10/2009 | Bacher et al. |
| 2010/0022837 | A1 | 1/2010 | Ishiguro et al. |
| 2010/0030020 | A1 | 2/2010 | Sanders et al. |
| 2010/0249497 | A1 | 9/2010 | Peine et al. |
| 2010/0268268 | A1 | 10/2010 | Bacher et al. |
| 2010/0298642 | A1 | 11/2010 | Trusty et al. |
| 2011/0009694 | A1 | 1/2011 | Schultz et al. |
| 2011/0112517 | A1 | 5/2011 | Peine et al. |
| 2011/0264129 | A1 | 10/2011 | Holdgate et al. |
| 2011/0306831 | A1 | 12/2011 | Kohnke et al. |
| 2011/0306841 | A1 | 12/2011 | Lozman et al. |
| 2012/0116362 | A1 | 5/2012 | Kieturakis |
| 2014/0073855 | A1 | 3/2014 | Kindler |
| 2014/0142377 | A1 | 5/2014 | Yang et al. |
| 2014/0148759 | A1 | 5/2014 | MacNamara et al. |
| 2014/0206936 | A1 | 7/2014 | Cooper et al. |
| 2014/0221749 | A1 | 8/2014 | Grant et al. |
| 2014/0243615 | A1 | 8/2014 | Schaeffer et al. |
| 2014/0275763 | A1 | 9/2014 | King et al. |
| 2014/0316203 | A1 | 10/2014 | Carroux et al. |
| 2014/0336532 | A1 | 11/2014 | Seguy |
| 2015/0282701 | A1 | 10/2015 | Oskin et al. |
| 2015/0366436 | A1 | 12/2015 | Henrick |
| 2016/0095585 | A1 | 4/2016 | Zergiebel et al. |
| 2016/0348769 | A1 | 12/2016 | Siegal |
| 2018/0203316 | A1 | 7/2018 | Xu |
| 2018/0203317 | A1 | 7/2018 | Li et al. |

FOREIGN PATENT DOCUMENTS

| | | |
|---|---|---|
| CN | 1956684 A | 5/2007 |
| CN | 101513338 A | 8/2009 |
| CN | 102871636 | 1/2013 |
| CN | 103505176 | 1/2014 |
| CN | 203506676 U | 4/2014 |
| CN | 203885470 | 10/2014 |
| CN | 204120980 U | 1/2015 |
| EP | 0567146 A2 | 10/1993 |
| EP | 1484003 A1 | 12/2004 |
| EP | 1561413 A1 | 8/2005 |
| JP | H0910166 A | 1/2014 |
| WO | WO2005112806 A2 | 12/2005 |
| WO | WO2008033356 A2 | 3/2008 |
| WO | WO2008045374 A2 | 4/2008 |
| WO | WO2008061106 A1 | 5/2008 |
| WO | WO2010066789 A1 | 6/2010 |
| WO | WO2010066790 A1 | 6/2010 |
| WO | WO2013071938 A1 | 5/2013 |
| WO | WO2013106444 A1 | 7/2013 |
| WO | WO2014127780 A1 | 8/2014 |

OTHER PUBLICATIONS

International Search Report for PCT/DK2016/050148 dated Aug. 11, 2016, 5 pages.
Written Opinion ISA for PCT/DK2016/050148 dated Aug. 10, 2016 in European Register, 46 pages.
Examination report in related Chinese Application No. 2016800390902 dated Dec. 11, 2018, 9 pgs.
Examination report in related Chinese application No. 2016800390902 dated Jul. 15, 2019, 4 pgs., including summary translation from Chinese counsel.

* cited by examiner

ENDOSCOPE

CROSS-REFERENCE TO RELATED APPLICATIONS

This is a § 371 application of International Application Number PCT/DK2016/050148, filed May 26, 2016, which claims priority from Denmark Patent Application Number PA 2015 70323, filed May 27, 2015, both applications incorporated herein by reference in their entirety.

The following applications disclose related subject matter: U.S. patent application Ser. No. 15/576,812, issued as U.S. Pat. No. 10,646,107 on May 12, 2020; U.S. patent application Ser. No. 15/576,813, issued as U.S. Pat. No. 10,631,716 on Apr. 28, 2020; U.S. patent application Ser. No. 15/576,814, issued as U.S. Pat. No. 10,624,531 on Apr. 21, 2020; U.S. patent application Ser. No. 15/576,815, issued as U.S. Pat. No. 10,617,284 on Apr. 14, 2020; U.S. patent application Ser. No. 15/576,816, issued as U.S. Pat. No. 10,645,260 on May 5, 2020; U.S. patent application Ser. No. 15/576,817, issued as U.S. Pat. No. 10,624,617 on Apr. 21, 2020; U.S. patent application Ser. No. 16/839,991, filed Apr. 3, 2020; and U.S. patent application Ser. No. 16/860,831, filed Apr. 28, 2020.

The present invention relates to endoscopes in general and more specifically to a means for maintaining a tensioned pull-wire in an endoscope.

Endoscopes are well known devices for visually inspecting inaccessible places such as human body cavities. Typically, the endoscope comprises an elongated insertion tube with a handle at the proximal end as seen from the operator and visual inspections means, such as a built in camera, at the distal end of the elongated insertion tube. This convention of distal and proximal, proximal being the end closest to the operator and distal being the end remote from the operator, as used above for the endoscope in general will, where applicable, be adhered to for all parts throughout this description. Electrical wiring for the camera and other electronics such as LED lighting run along the inside of the elongated insertion tube from the handle to the tip at the distal end. Instead of using cameras, endoscopes may also be fiber-optic, in which case the optical fibers run along inside of the elongated insertion tube. Also, a working channel may run along the inside of the insertion tube from the handle to the tip, e.g. allowing liquid to be removed from the body cavity or allowing the insertion of surgical instruments or the like into the body cavity.

Furthermore, in order to be able to maneuver the endoscope inside the body cavity, the distal end of the endoscope may comprise a section with increased flexibility, e.g. an articulated tip part allowing the operator to bend this section. Typically this is done by tensioning or slacking pull-wires in a guide tube also running along the inside of the elongated insertion tube from the articulated tip part to a control mechanism with an operating member in the handle in an arrangement commonly known as a Bowden cable, cf. Bowden's original U.S. Pat. No. 609,570.

The pull-wire running along the inside of the guide tube of a Bowden cable normally extends with a predetermined length over either end allowing an operating member to be attached to a free end, in the following referred to as the proximal end, and an operated member to attached to the other free end, in the following referred to as the distal end. When the ends of the guide tube are held stationary, movement of the proximal end of the pull-wire with respect to the guide tube is transmitted to the distal end as a corresponding movement of the distal end of the pull-wire with respect to the guide tube, so as to effect a movement of the operated member.

It is a known in the art to provide a mechanical member holding the proximal end of guide tube in endoscopes. For instance U.S. Pat. No. 4,203,430 discloses an arrangement where the proximal ends of the pull-wires are terminated in internally threaded adjustment cylinders. Generally, the fastening of the proximal end of the guide tube to the operating handle is achieved with mechanical means where the guide tube is clamped or terminated in a block member, which however contributes to increasing the number of part required to assembly the control mechanism of the endoscope.

Based on this prior art it is the object of the present invention to provide an endoscope, preferably a disposable endoscope, which reduces the amount of mechanical parts required to assemble the control mechanism.

According to a first aspect of the invention this is achieved with an endoscope having an operating handle comprising a handle housing arranged at a proximal end thereof and an insertion tube extending from said handle towards a distal end of the endoscope and terminating in a steerable tip part at the distal end of the endoscope, the endoscope further comprising a control mechanism with a Bowden cable having an outer guide tube having a first length between a proximal end and a distal end of said outer guide tube and an inner pull-wire having a second length between a proximal end and a distal end of said inner pull-wire, said second length being longer than said first length, the proximal end of the outer guide tube is affixed to the operating handle by means of an adhesive. This allows for a simple and practical configuration and assembly of the Bowden cable arrangement and the required number of parts and costs to obtain good bending properties of the distal tip by adhering a portion of the outer surface of the outer guide tube to the operating handle. Furthermore, the utilized adhesive used as assembly means is already at hand for assembly of other parts of single use endoscopes.

In a further preferred embodiment the endoscope further comprises a working channel extending from the operating handle to the tip part, the outer guide tube is affixed by means of an adhesive to the working channel at at least one point between the operating handle and the tip part. This configuration has shown to increase the bending properties at the distal tip while still reducing the number of mechanical parts and costs for assembly of the Bowden cable arrangement.

In a further embodiment that facilitates assembly of the endoscope, the adhesive is a reactive adhesive, preferably an UV adhesive.

In yet a further embodiment an inner surface of the operating handle is provided with a first recess wherein the outer guide tube is positioned and affixed by means of the adhesive. This ensures a correct position of the Bowden cable arrangement with respect to other mechanical and movable parts inside the operating handle. It furthermore allows correct and precise application of the correct amount of adhesive as the position is readily indicated to the operator at the assembly line.

In a further improved practical embodiment the recess has a length and the adhesive is located in the most distal ⅔ of the length of the recess. This allows correct mounting and fastening of the outer guide tube when these are cut to various lengths, i.e. small tolerances of the outer guide tube length can be accepted.

In a further embodiment the inner surface of the operating handle comprises a second recess for receiving the on outer guide tube of a second Bowden cable and in that the recesses are located in the same side of the operating handle. This provides an improved bending range of the distal tip as a second Bowden cable arrangement may be provided, while a practical guidance of the pull-wires towards the operating member is ensured.

In a further improved embodiment the operating handle has a height and that a proximal end of the first recess is located at a higher height than a proximal end of the second recess. This ensures even further improved and space utilising guidance of the pull-wires towards the operating member allowing room and operating space for other movable mechanical parts inside the operating handle.

Figure 1A:
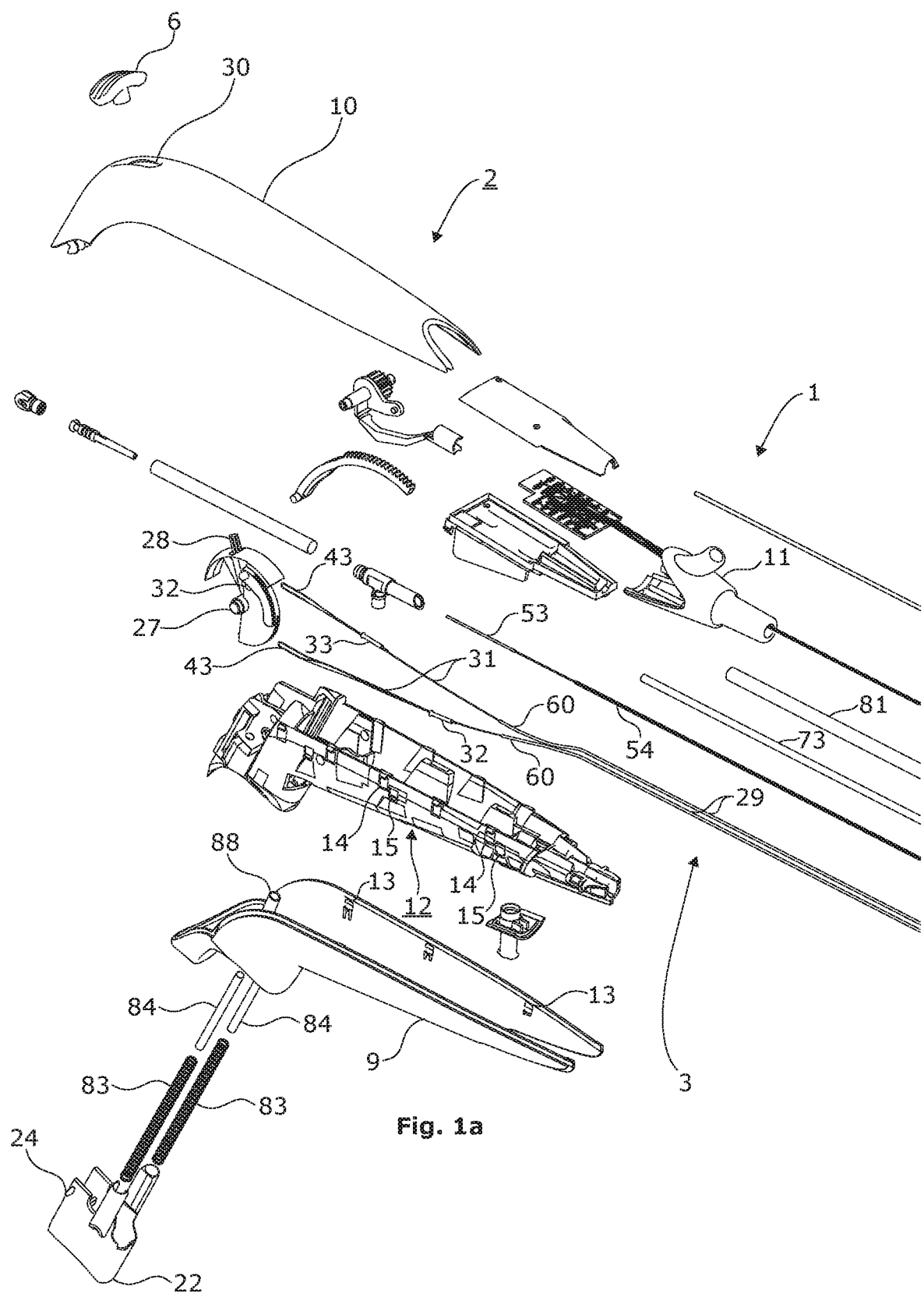
Figure 1B:
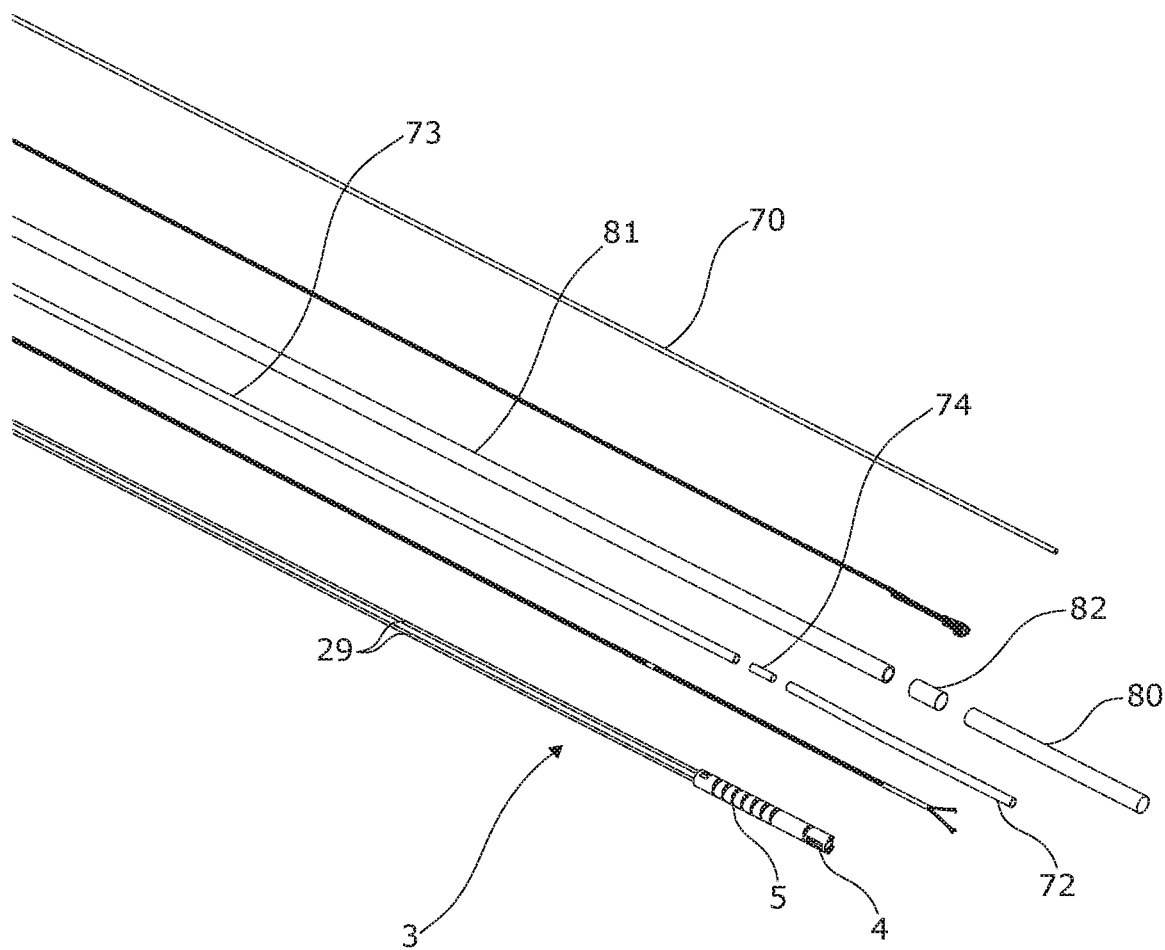
Figure 2:
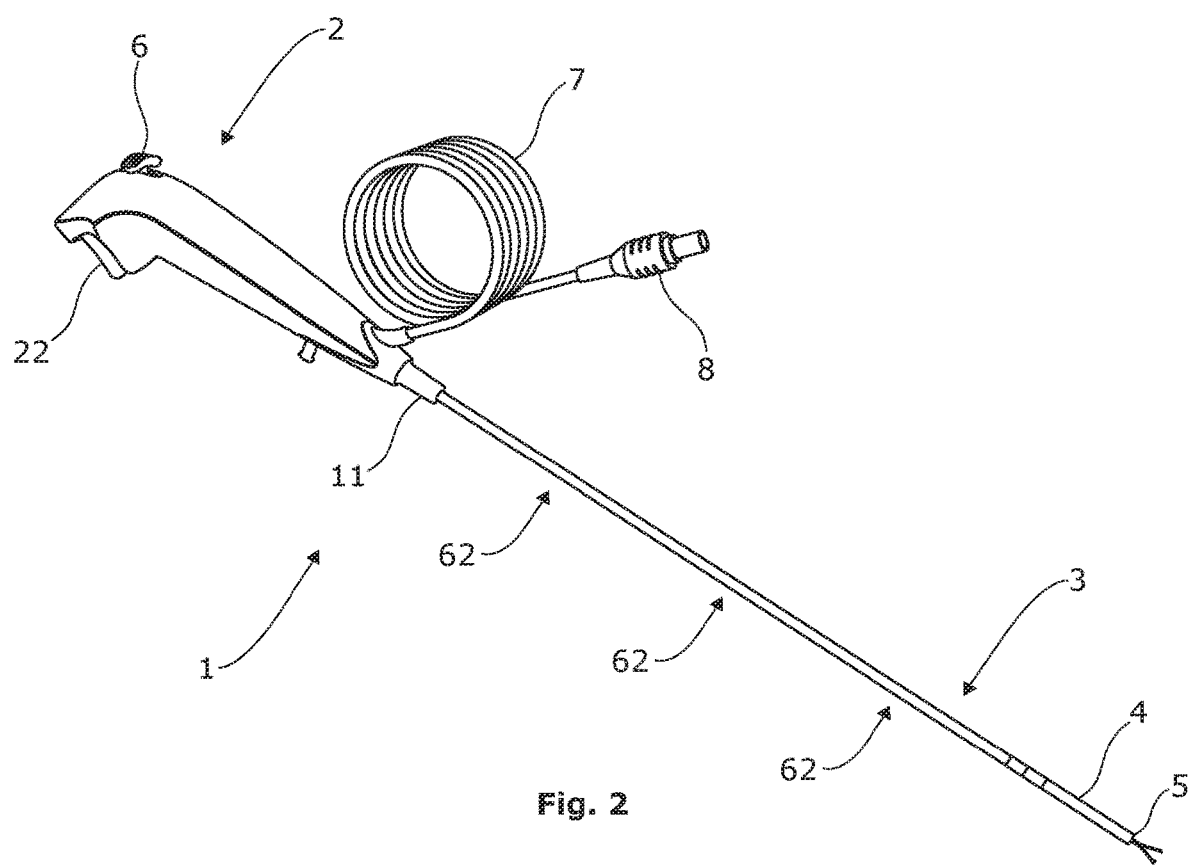
Figure 3:
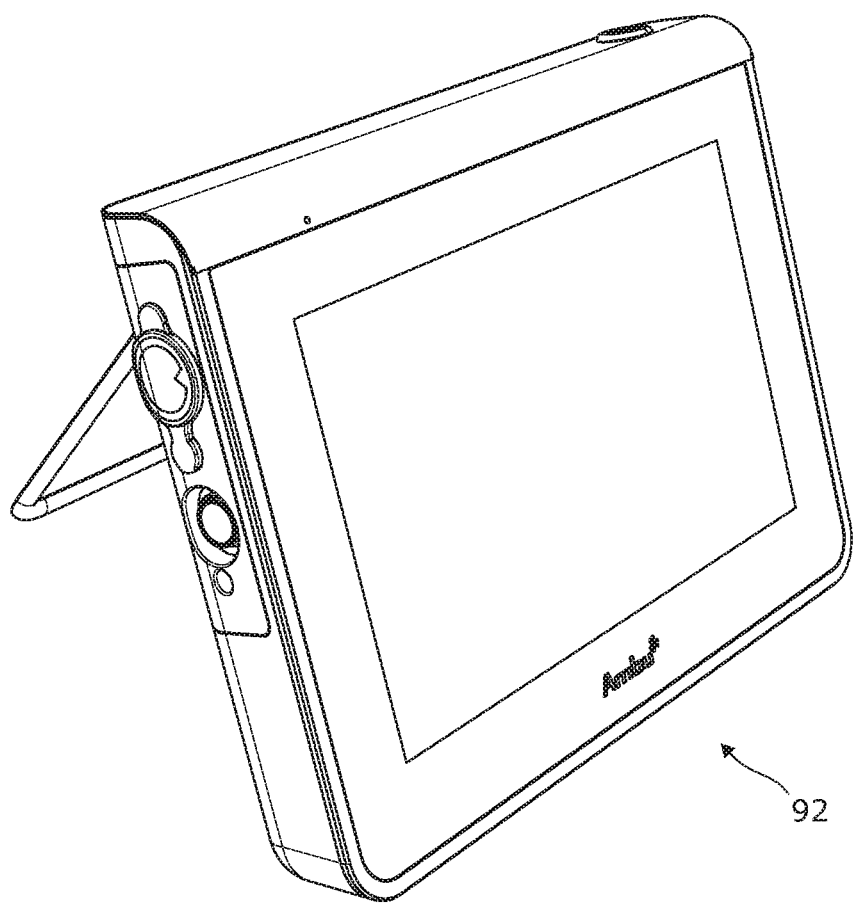
Figure 4:
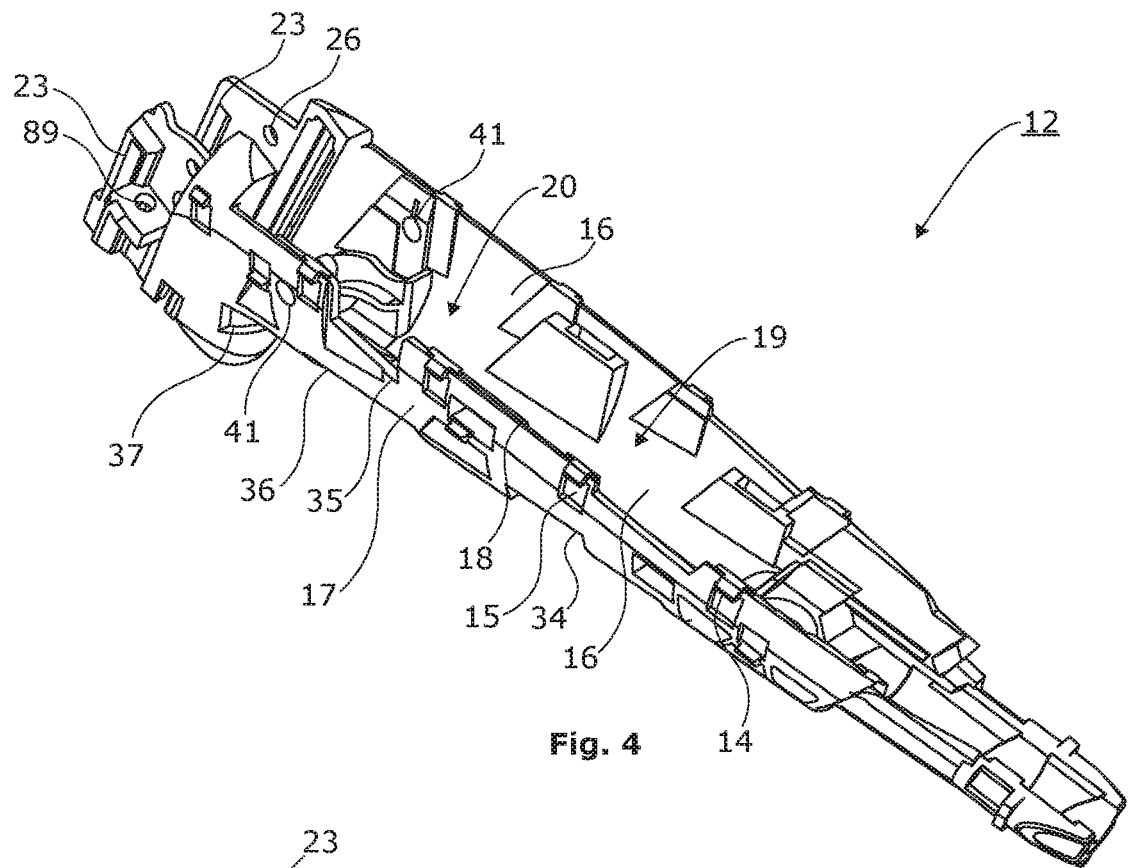
Figure 5:
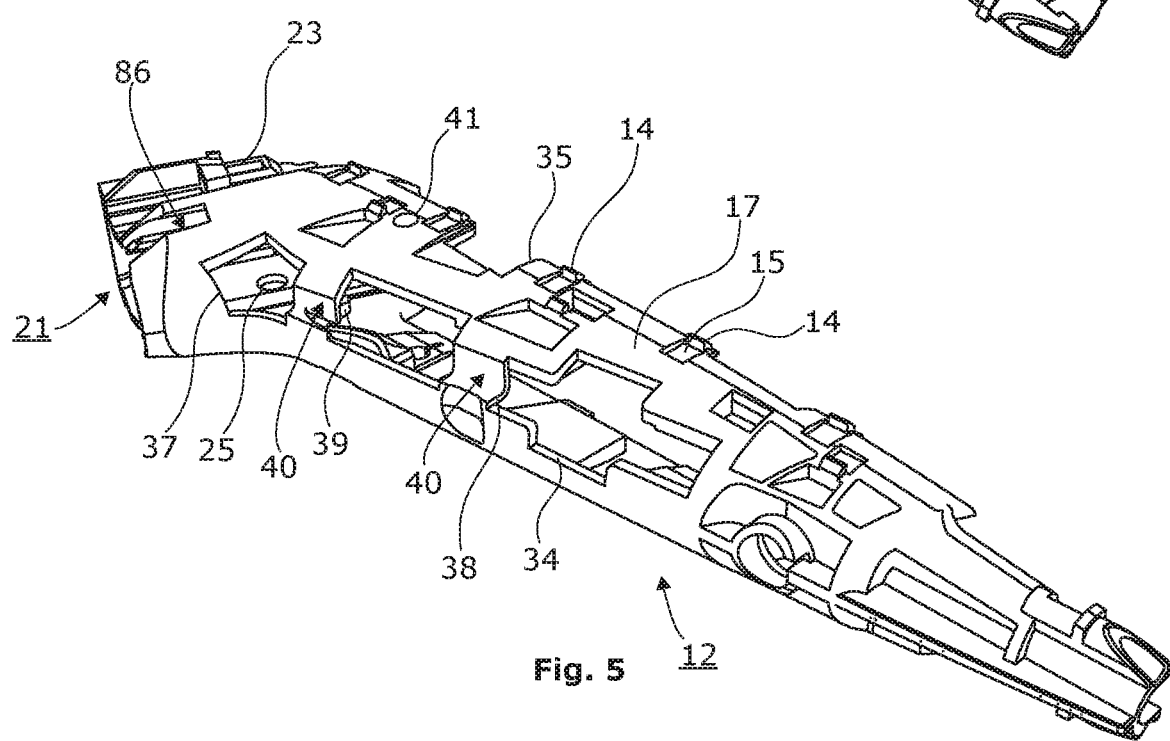
Figure 6:
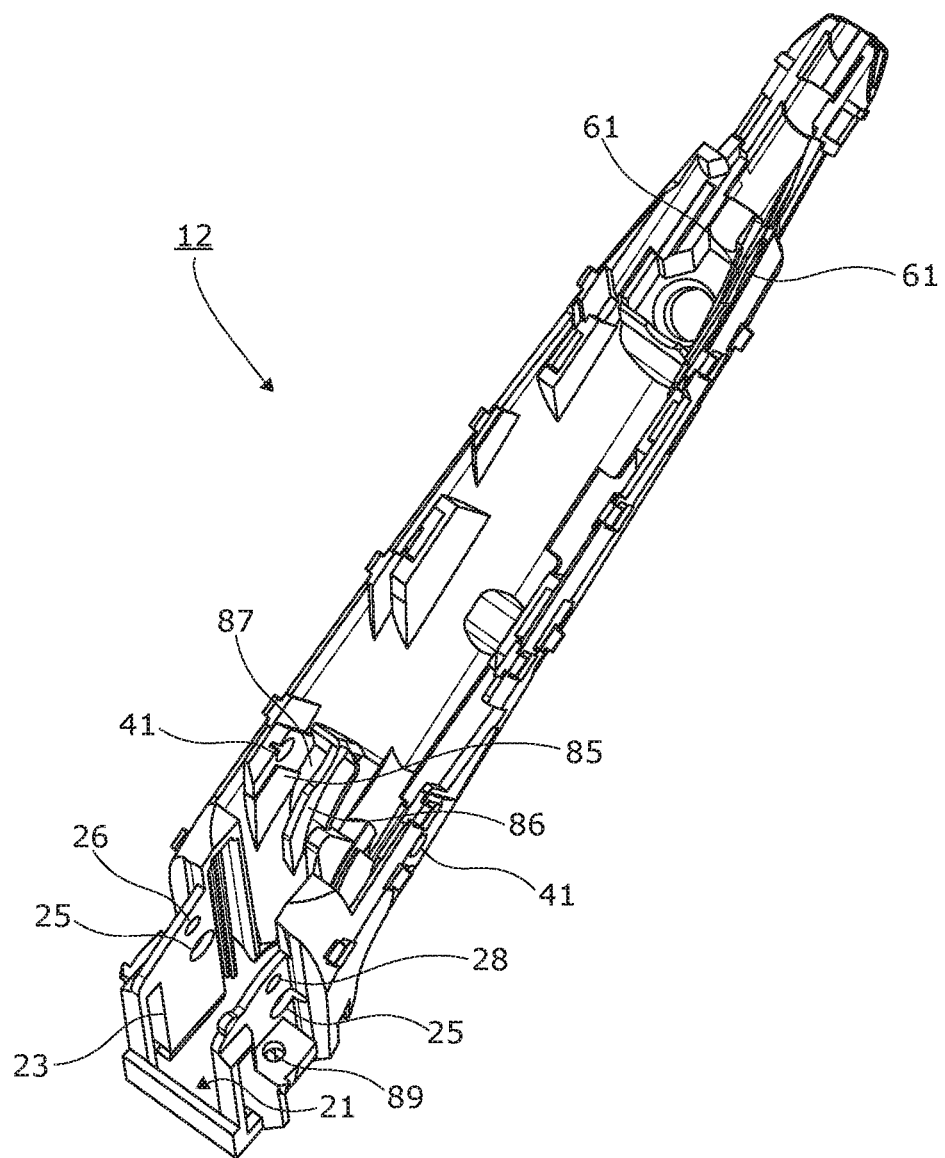
Figure 7:
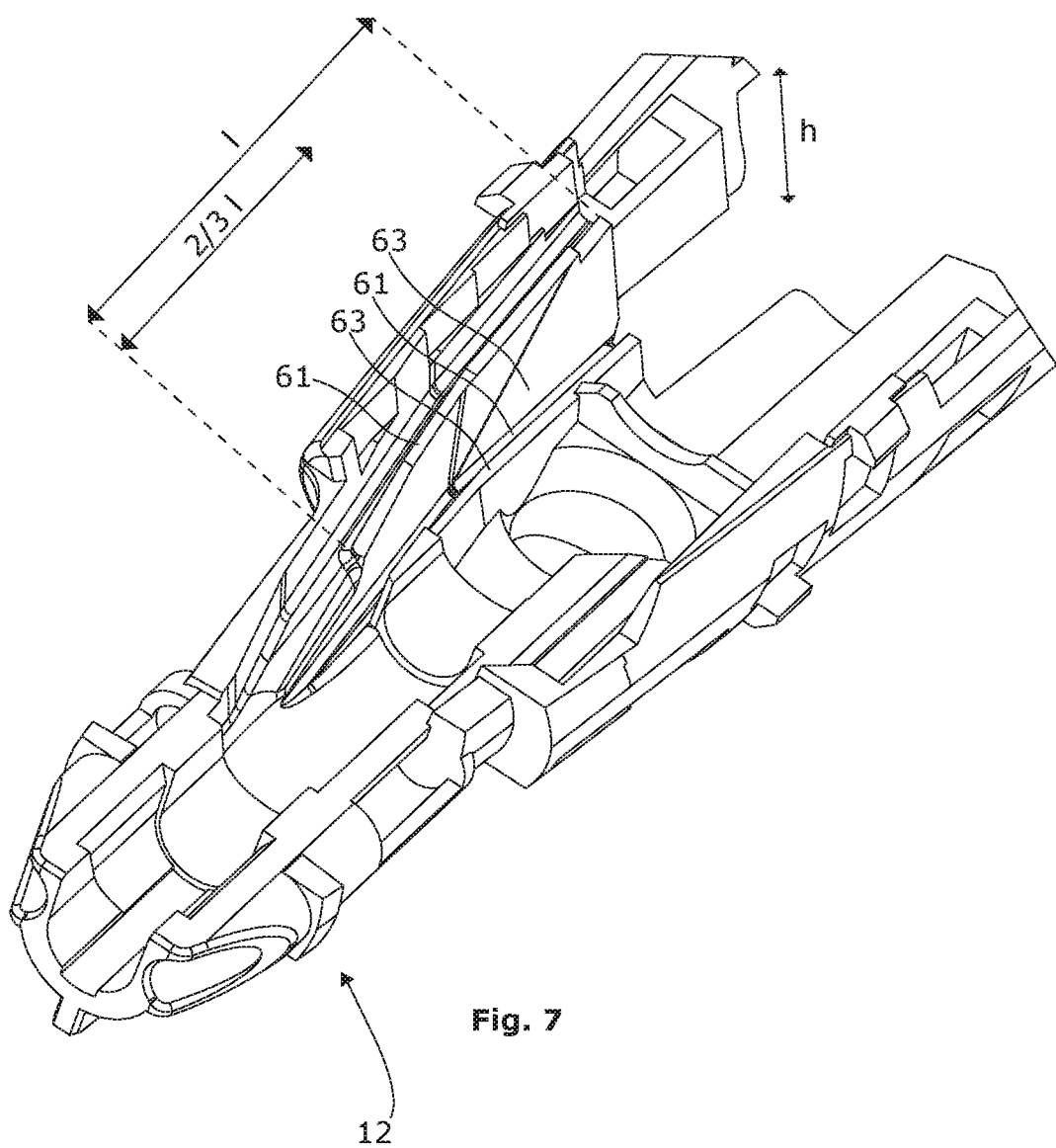
Figure 8:
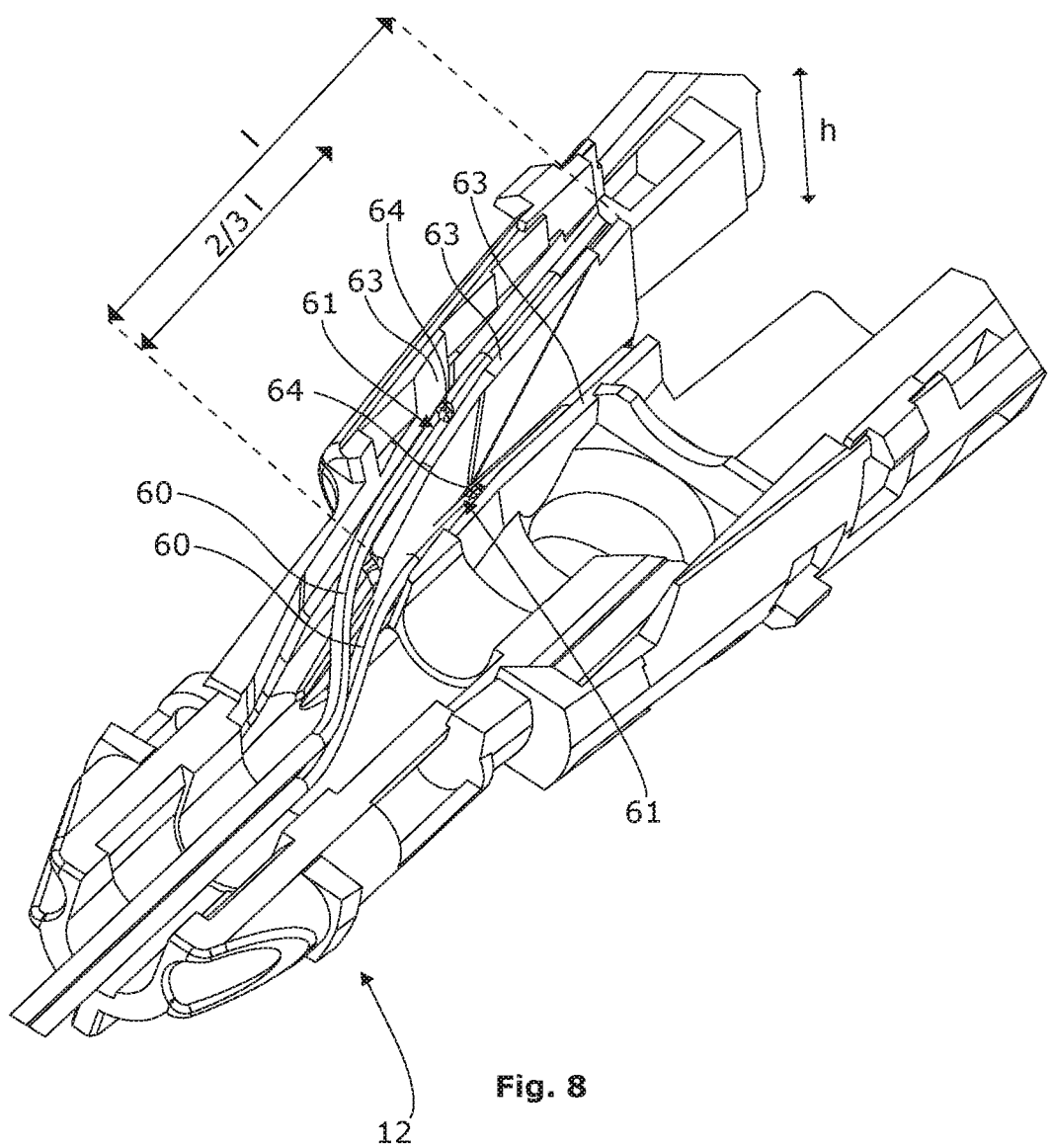

The invention will now be described in greater detail based on nonlimiting exemplary embodiments and with reference to the drawings, on which:

FIG. 1 shows an overview of an endoscope according to the present invention and how this exploded view is split in a left-hand side part and a right hand side part for better visibility in FIG. 1a and FIG. 1b, FIG. 2 shows a perspective view of the fully assembled endoscope of FIG. 1, FIG. 3 shows a monitoring device adapted for mutual connection with the endoscope of FIG. 1, FIG. 4, FIG. 5 and FIG. 6 show perspective views of a chassis of the endoscope of FIG. 1, FIG. 7 shows a different perspective view of details of the left-hand side of the handle part of FIG. 4, FIG. 8 shows a preferred use of the embodiment shown in FIG. 7.

Turning first to FIG. 2 an assembled endoscope 1 according to the present invention is shown. The endoscope 1 has a proximal end with an operating handle 2 to be held in one hand by an operator. Accordingly, the operating handle is shaped in a manner ergonomically suitable for operator, in particular but not exclusively for the hand of the operator, as arms and joints may also play a role in the ergonomics. From the handle 2 an insertion tube 3 extends towards the distal end of the endoscope. At the distal end of the endoscope 1 the insertion tube 3 ends in a bending section 4 and a tip part 5. The bending section 4 is in mechanical connection with an operating member 6, digitally operable by the operator, e.g. by the thumb, thereby allowing the operator to bend the tip part 5 in a desired direction when advancing the insertion tube 3 towards a desired location, e.g. through a body cavity of a patient. As can also be seen the endoscope 1 comprises a flexible connection cable 7 with a connector 8 allowing the endoscope 1 to be connected to a monitoring device such as a monitor 92 shown in FIG. 3 forming part of an endoscope 1 and monitor 92 system.

Turning now to FIGS. 1, 1a and 1b an exploded view of the endoscope 1 is shown. As mentioned, the endoscope 1 has an operating handle 2 at the proximal end thereof i.e. at the left-hand side of FIG. 1. The operating handle 2 is assembled from and comprises a number of handle parts to be described later. From the operating handle 1, the insertion tube 3 comprising a number of insertion tube parts to be described later extends towards the distal end of the endoscope, i.e. towards the right-hand side of FIG. 1.

The operating handle 2 comprises at least two shell parts 9, 10 forming the outer housing walls of the handle housing of the operating handle 2. The two shell parts 9, 10 form the outer housing walls and are shaped to provide an ergonomically suitable operating handle for an operator, gripping it with one hand. In addition to the two shell parts 9, 10 a transition part 11 forming the transition from the operating handle to the insertion. Turning now to FIGS. 1, 1a and 1b an exploded view of the endoscope 1 is shown. As mentioned, the endoscope 1 has an operating handle 2 at the proximal end thereof i.e. at the left-hand side of FIG. 1a. The operating handle 2 is assembled from and comprises a number of handle parts to be described later. From the operating handle 1, the insertion tube 3 comprising a number of insertion tube parts to be described later extends towards the distal end of the endoscope, i.e. towards the right-hand side of FIG. 1b.

The two shell parts 9, 10 are adapted to engage and be held and be supported by a chassis 12, in turn, adapted to support said at least two shells parts 9, 10 by suitable engagement means, such as recesses and/or protrusions 13 interlocking with suitable complementary means 14, 15 on the chassis 12, better visible in FIGS. 4 and 5. Furthermore the shell part 10 has pair of columns 88 of which only one is visible in FIG. 1a. These columns 88 serve the attachment of the shell part 10 to the chassis 12. The shell part has internal engagement means (not visible) at adapted to engage the shell part 9 at the proximal end of the endoscope 1, so as hold them together. At the other end the shell parts are held together by the transition part 11.

Turning now to the FIGS. 4, 5 and 6 the chassis 12 will be described in greater detail. The chassis 12 preferably shell shaped, i.e. said chassis comprises an essentially shell shaped structure with a shell wall having an inner surface 16 and an outer surface 17 linked by an edge 18, said essentially shell shaped structure defining an interior compartment 19 delimited by said inner surface 16 and the edge 18 of the shell wall, the edge thus defining main opening 20 of said interior compartment 19. It will be understood that the chassis 12 can be designed mainly based on technical requirements, such as kinematic chains of movable parts, and thus be optimized for those technical requirements without having to inherit constraints from the ergonomic requirements of the handle 2, i.e. the shape of the two shell parts 9, 10.

Best visible in FIGS. 4 and 5 are a number of different apertures and cut-outs formed in the chassis 12. These apertures form vias for different purposes between the interior compartment 19 and the exterior of the chassis 12.

The different cut-outs and apertures differ in shape, size, location and lay-out depending on their purposes, and may as mentioned be designed according to technical requirements, independently of the ergonomic requirements of the handle 2.

Starting from the proximal end of the endoscope 1 there is an aperture 21, as best seen in FIG. 6. The aperture 21 accommodates a push button 22, so that the push-button 22 extends from the interior compartment of the chassis 12 to the exterior, and on through an aperture in the shell part 9 to be accessible by an operator holding the handle 2 of the endoscope 1. The push-button 22 is preferably biased towards an external position by means of two coil springs 83 guided by two guiding columns 84 fixed in the bottom two wells provided in the chassis 12, preferably by gluing using UV-curable glue or resin transmitted through the transparent material of the chassis 12. The two guiding columns 83 further serve to reduce friction between the coil springs 83 and the columns 88. They are therefore preferably made of a material with relatively low friction, such as low-density polyethylene LDPE, e.g. Cosmothene® 4812.

On the outer surface 17 of the shell wall of the chassis 12 two lugs with holes 89 are provided. These serve to engage the columns 88 on the shell part 10 for attaching it to the chassis, as described above.

In the shell wall two elongate apertures 23 in the form of slits are provided. The two elongate apertures 23 are preferably arranged as a pair, one on either side of the aperture 23. The two elongate apertures 23 serve as guide means for the push-button by accommodating a respective protrusion 24 provided on the surface of the push-button 22.

In the vicinity of the two elongate apertures 23, a first and a second pair of apertures 25, 26 in the form of essentially cylindrical through holes are provided. The first pair of essentially cylindrical apertures serve as pivotal bearings for trunnions 27 of a control lever 28 for maneuvering the bending section 5 via an arrangement of a pair of Bowden pulls 29. As can best be seen in FIGS. 1 and 2, the control lever 28 is attached to the control knob 6, and at least the control knob extends to the outside of the endoscope handle 2 through a slit 30 in the shell part 10 to be accessible by a thumb of the an operator. It should be noted that it is not essential for the function as bearings for the trunnions 27 of the control knob, that the holes are though holes, but because the chassis is preferably injection moulded, through holes may be much easier manufactured than e.g. blind holes.

The second pair of apertures 26 are preferably also circular through holes and have the same diameter. They need not be circular, however, as their purpose is allowing the insertion of a tool, such as a rod in order to immobilise the control lever 28 during assembly of the endoscope, more specifically when attaching the proximal ends of the pull wires 31 of the two Bowden pulls 29 to the control lever 28. Accordingly, the control lever 28 has a through hole 32, corresponding in size to the apertures 26, and adapted to align with these in one position of the control lever 28, thereby allowing the insertion of the tool through all three holes, 26, 32, so as to block movement of the control lever 28 with respect to the chassis 12. The position of the three holes 26, 32 are selected so as to block the control lever 28 in a position later corresponding to a neutral position of the control lever 28 and knob 6, in which the bending section 4 is straight.

With the control lever 28 blocked during assembly the cables 31 Bowden pull may be attached to the control lever 28 in a well defined manner. This is preferably done by threading the respective free end of each cable 31 through suitable passages in the control lever 28, forming a loop 43 by looping the free ends back to the respective cable and crimping the free end onto the cable 31 using a barrel 33. The barrel 33 may be of the open barrel type, to avoid the hazel of sliding the barrel 33 on onto the cable 31 prior to crimping. Evidently, other attachments for the loop 43, such as protrusions, may also be used. Furthermore, entirely different attachments methods without loops are also envisaged, albeit not preferred.

To facilitate this assembly process a cross-shaped aperture 34 is located in the vicinity of the bottom of the chassis 12, i.e. away from the main opening 20 defined by the edge 18. Likewise a cut-out 35 in the wall from the edge 18 is provided. The cross-shaped aperture 34 and the cut-out 35 allows access to the cables 31 various tools, such as holding and crimping tools during the assembly.

As can best be seen in FIG. 5 the cross-shaped aperture 34 a further, essentially rectangular aperture is generally aligned with a further rectangular access aperture 36 and a pentagonal aperture 37 in the direction towards the proximal end of the endoscope 1. The cross-shaped aperture 34, the rectangular aperture 36 and the pentagonal aperture 37 are separated by respective bridges 38 and 39. These bridges 38, 39 do not follow the general curvature of the outer surface 17 of the chassis 12 but are indented to form a generally V-shaped groove 40 connecting the cross-shaped aperture 34 to the pentagonal aperture 37 via the rectangular aperture 36. As can be seen from FIG. 7, this V-shaped groove 40 in the outer surface 17 provides the outer surface 17 with a means for guiding one or more movable parts, in particular the cable 31 of the Bowden pull between two apertures, such as the cross-shaped aperture 34 and the pentagonal aperture 37 along the outer surface 17 outside of the interior compartment 19. This in turn allows the unsupported free end of the pull wire 31 of the Bowden pull arrangement to follow a straight line. At the same time, because the unsupported free end of the pull wire 31 passes from the interior compartment 19 of the chassis 12 to the exterior via the cross-shaped aperture 34, the pull wire 31 becomes easily accessible for the assembly tools, in particular the crimping tool. The cross-shape of the cross-shaped aperture, in turn, facilitates the use of the tools by providing the necessary space for opening and closing the tools, be it a crimping tool or a holding tool.

In FIGS. 4 and 5 a further pair apertures 41 in the form of essentially cylindrical through holes can be seen. Similar to the apertures 25, the further pair of apertures 41 serve as bearings of trunnions 42 carrying a pinion 44. The pinion 44 is adapted to be in engagement with a curved rack 45 having a first free end 46 and a second end with trunnions 47 held loosely in suitable receptacles inside the push button 22. The rack 45 as such is loosely held in a guideway comprising a first side 85, a second side 86 and a curved bottom 87 adapted to keep the rack 45 in engagement with the pinion 44, cf. FIG. 6. The first side 85 and the second side 86 as well as the curved bottom 87 are preferably formed integrally with the remainder of the chassis 12, e.g. in an injection moulding process. The first side is preferably constituted by a plane surface of a thickened part of the wall, i.e. a raised part of the inner surface 16 of the chassis 12.

The entire insertion tube 3 is sealingly encapsulated in a flexible outer tube. The outer tube comprises a first outer tube section 80 and a second outer tube section 81 joined with a sleeve 82. The first outer tube section 80 is more flexible than the second tube section 81 in order to comply with the movements of the bending section 5. The second tubular member 73 is however still quite flexible. More specifically, the second tubular member 73 and a second outer tube section 81 surrounding it are so flexible that they allow a loose knot to be tied on the insertion tube 3. The alternative is a rigid or semi-rigid endoscope where the insertion portion is rigid, only slightly bendable or hinged, and which does not allow a knot to be tied on the insertion tube. Starting from the distal end of the insertion tube 3 there is provided a working channel formed by a first tube segment 72 attached to and preferably embedded in the tip part 4 at one end. The second end of the first tube segment 72 is connected to a first end of a second tube segment 73 by means of a short length of rigid tubing 74. Rigid in this sense is to mean more rigid than the second tube segment 73 which, in turn, is more rigid than the first tube segment 72 which has to comply with the flexibility requirements of the bending section 5

A transparent plastic material is advantageous in that it more efficiently allows dispersion of light and hence better allows parts to be joined and/or sealed using an UV curable glue or resin, i.e. an adhesive that hardens under the influence of ultraviolet light. In respect of glue or resin, be it UV curable or not, it has been found that simply gluing the proximal end portions of the outer guide tubes 60 of the Bowden pulls 29 to the operating handle is sufficient to secure the Bowden pulls 29 in position. Hence it has been realised that in a simply cost reducing and efficient embodiment of a single use endoscope, an outer surface of the outer guide tubes 60 can be adhered to the operating handle in order to secure the Bowden pulls 29 in position. I.e. a part of the outer surface of the outer guide tube adjacent to the most proximal part of the outer guide tube is adhered to the operating handle. This is primarily, because, as it has been realized, adjustment is not needed. Adjustment, in turn, is not necessary because any slacking of the pull-wire 31 of the Bowden pull 29 is negligible in a disposable endoscope 1. The pull-wires 31 are not under any substantial tension during shelf life and will hardly undergo any mentionable stretching during the one short occasion the disposable endoscope 1 is in use. Preferably, the outer guide tubes 60 are made of a coiled wire. Preferably a coiled stainless steel wire, which also has shown to hardly undergo any stretching during shelf life and use as required for a single-use endoscope.

FIG. 7 shows in more detail the recesses 61 provided along the inner surface of the operating handle 2. In the embodiment shown recesses 61 are provided in a chassis 12 which is a part of the operating handle. Evidently, the recesses may be provided on the inner surfaces of the shell parts 9, 10 forming the shell structure of the operating handle 2. Likewise, the proximal end of the outer guide tubes 60 of the Bowden pulls 29 may be glued directly to the operating handle without the provision of recesses 61. The recesses 61 are provided in one side of the operating handle 2 and are formed by upright standing wall sections 63 forming the elongate recesses 61 extending in the proximal-distal longitudinal direction of the operating handle 2, wherein the outer guide tubes are positioned as shown in FIG. 8. The recesses 61 may share a wall section 63 and the side wall of the operating handle may form part of the recesses 61. The recesses 61 are elongate with a length l as indicated in FIGS. 7 and 8. To keep the outer guide tubes 60 in the desired position in the recesses 61 they are adhered and thereby affixed to the recesses, preferably the adhesive is an UV curable glue or resin, i.e. one that hardens under the influence of ultraviolet light. Dots of applied adhesive 64 are indicated in FIG. 8. It is preferred that the adhesive is applied in the most distal ⅔ of the recesses indicated with ⅔ l in FIGS. 7 and 8. This provides more tolerance to the length of the outer guide tubes and ensures that they are affixed to the operating handle even if they are provided to the shorter side within the tolerances. Evidently, the adhesive may be applied in many different manners as long as it serves the purpose of affixing the outer guide tube 60 to the operating handle 2 so that the pull-wire may be keep its tension during self-life and use. Hence the adhesive may be applied before or after the outer tube is positioned as desired and even application of adhesive both before and after positioning of the outer guide tube is possible.

As indicated with h in FIGS. 7 and 8 the operating handle 2 has a height h and the proximal end of the two recesses 61 are located at different locations along the height h. Thereby the recesses also serves a guide means of the pull-wires 31 towards the control lever 28. As indicated in FIG. 1a this is desirable because the pull-wires 31 are fastened to the control lever 28 at different heights.

It has also shown advantageous to adhere the outer guide tubes 60 of the Bowden pulls 29 to an outer surface of the working channel in order to improve the bending properties of the distal tip 4. This is indicated in FIG. 2 where 62 indicated points where the guide tube is affixed to the working channel by means of an adhesive, preferably to the second tubular member 73. In the embodiment three points between the operating handle and the bending section 4 are indicated, but at least one point would suffice. Again an UV curable glue or resin, i.e. an adhesive that hardens under the influence of ultraviolet light, which is used for gluing other parts of the operating handle, and especially the proximal ends of the outer guide tubes to the operating handle, is suitable as adhesive to glue the parts together.

The embodiments described in the above description of how to implement the solutions of the invention are only examples. The skilled person will realize that numerous variations to the solutions may be presented without departing from the scope of the invention. In particular, the solutions may be implemented in endoscopes differing in construction from those used in the exemplary embodiments. Also, the skilled person will realize that e.g. material choices and dimensions may vary. The skilled person will also understand that the above description of the exemplary embodiments refer to those embodiments in a neutral relaxed state, i.e. when the endoscopes are not in use, and not influenced by external forces.

What is claimed is:

1. An endoscope comprising:
an operating handle including a handle housing having a proximal end and a distal end opposite the proximal end, and disposed within the handle housing, a first wall, a second wall substantially parallel to the first wall and defining a first elongate recess therebetween, a third wall, and a second elongate recess between the second wall and the third wall;
an insertion tube extending from the distal end of the handle housing and terminating in a steerable tip part; and
a control mechanism including a first Bowden cable and a second Bowden cable, the first Bowden cable having a first outer guide tube having a first length between a proximal end and a distal end of the outer guide tube and a first inner pull-wire having a second length between a proximal end and a distal end of the first inner pull-wire, the second length being longer than the first length, and the second Bowden cable having a second outer guide tube and a second inner pull-wire,
wherein a portion of the first outer guide tube is positioned in the first elongate recess and affixed to the first elongate recess with an adhesive, and
wherein a portion of the second outer guide tube is positioned in the second elongate recess and affixed to the second elongate recess with the adhesive,
wherein the control mechanism includes a steering control lever defining a rotation plane that traverses a first external surface and a second external surface of the handle housing, the first external surface being opposite and spaced apart from the second external surface and including a slit through which a portion of the steering control lever protrudes, and wherein a proximal end of the first elongate recess is located closer to the first external surface than a proximal end of the second elongate recess.

2. The endoscope of claim 1, further comprising a working channel extending from the operating handle to the tip part, wherein the first outer guide tube is affixed with the adhesive to the working channel at at least one point between the operating handle and the tip part.

3. The endoscope of claim 1, wherein the first elongate recess has a length and the adhesive is located in a most distal ⅔ of the length of the first elongate recess.

4. The endoscope of claim 1, wherein the operating handle further comprises a chassis disposed within the handle housing and having a shell structure, the chassis including the first wall, the second wall, and the third wall.

5. The endoscope of claim 1, wherein the first wall has an inner surface connected to a bottom surface of the first elongate recess and the second wall has a first inner surface connected to the bottom surface of the first elongate recess and a second inner surface opposite the first inner surface and connected to a bottom surface of the second elongate recess.

6. The endoscope of claim 5, wherein the portion of the first outer guide tube affixed to the first elongate recess with adhesive is affixed to at least one of the inner surface of the first wall, the bottom surface of the first elongate recess, or the first inner surface of the second wall.

7. The endoscope of claim 6, wherein the portion of the second outer guide tube affixed to the second elongate recess with adhesive is affixed to at least one of the second inner surface of the second wall, the bottom surface of the second elongate recess, or an inner surface of the third wall.

8. The endoscope of claim 5, wherein the third wall has an inner surface connected to the bottom surface of the second elongate recess and facing the second inner surface of the second wall.

9. The endoscope of claim 5, wherein the control mechanism includes a steering control lever, and wherein the first elongate recess and the second elongate recess serve as guides for, respectively, the first inner pull-wire and the second inner pull-wire to align the first inner pull-wire and the second inner pull-wire with fastening points at the control lever.

10. The endoscope of claim 9, wherein the bottom surface of the first elongate recess and the bottom surface of the second elongate recess form an angle greater than 0 to align the first inner pull-wire and the second inner pull-wire with the fastening points at the control lever.

11. The endoscope of claim 1, wherein first wall, the second wall, and the third wall extend substantially in a proximal-distal direction.

12. The endoscope of claim 1, wherein the first wall and the second wall extend from the bottom surface of the first elongate recess a distance greater than a diameter of the first Bowden cable.

13. An endoscope comprising:
an operating handle including a handle housing having a proximal end and a distal end opposite the proximal end, and disposed within the handle housing, a first wall, a second wall substantially parallel to the first wall and defining a first elongate recess therebetween, a third wall, and a second elongate recess between the second wall and the third wall;
an insertion tube extending from the distal end of the handle housing and terminating in a steerable tip part; and
a control mechanism including a first Bowden cable and a second Bowden cable, the first Bowden cable having a first outer guide tube having a first length between a proximal end and a distal end of the outer guide tube and an inner pull-wire having a second length between a proximal end and a distal end of the inner pull-wire, the second length being longer than the first length, and the second Bowden cable having a second outer guide tube and a second inner pull-wire,
wherein a portion of the first outer guide tube is positioned in the first elongate recess and affixed to the first elongate recess with an adhesive, and
wherein a portion of the second outer guide tube is positioned in the second elongate recess and affixed to the second elongate recess with the adhesive, and
wherein the operating handle further comprises a chassis disposed within the handle housing and having a shell structure, the chassis including the first wall, the second wall, and the third wall.

14. The endoscope of claim 13, further comprising a working channel extending from the operating handle to the tip part, wherein the first outer guide tube is affixed with the adhesive to the working channel at at least one point between the operating handle and the tip part.

15. The endoscope of claim 13, wherein the control mechanism includes a steering control lever defining a rotation plane that traverses a first external surface and a second external surface of the handle housing, the first external surface being opposite and spaced apart from the second external surface and including a slit through which a portion of the steering control lever protrudes, and wherein a proximal end of the first elongate recess is located closer to the first external surface than a proximal end of the second elongate recess.

16. The endoscope of claim 13, wherein the first wall has an inner surface connected to a bottom surface of the first elongate recess and the second wall has a first inner surface connected to the bottom surface of the first elongate recess and a second inner surface opposite the first inner surface and connected to a bottom surface of the second elongate recess.

17. The endoscope of claim 16, wherein the third wall has an inner surface connected to the bottom surface of the second elongate recess and facing the second inner surface of the second wall.

18. The endoscope of claim 13, wherein the second wall is located between the first elongate recess and the second elongate recess intermediate the first wall and the third wall.

19. The endoscope of claim 13, wherein first wall, the second wall, and the third wall extend substantially in a proximal-distal direction.

20. An endoscope comprising:
an operating handle including a handle housing having a proximal end and a distal end opposite the proximal end, and disposed within the handle housing, a first wall, a second wall substantially parallel to the first wall and defining a first elongate recess therebetween, a third wall, and a second elongate recess between the second wall and the third wall;
an insertion tube extending from the distal end of the handle housing and terminating in a steerable tip part; and
a control mechanism including a first Bowden cable and a second Bowden cable, the first Bowden cable having a first outer guide tube having a first length between a proximal end and a distal end of the outer guide tube and a first inner pull-wire having a second length between a proximal end and a distal end of the first inner pull-wire, the second length being longer than the first length, and the second Bowden cable having a second outer guide tube and a second inner pull-wire,
wherein a portion of the first outer guide tube is positioned in the first elongate recess and affixed to the first elongate recess with an adhesive, wherein a portion of the second outer guide tube is positioned in the second elongate recess and affixed to the second elongate recess with the adhesive, wherein the operating handle further comprises a chassis disposed within the handle housing and having a shell structure, the chassis including the first wall, the second wall, and the third wall, wherein the first wall has an inner surface connected to a bottom surface of the first elongate recess and the second wall has a first inner surface connected to the bottom surface of the first elongate recess and a second inner surface opposite the first inner surface and connected to a bottom surface of the second elongate recess, wherein the control mechanism includes a steering control lever, and wherein the first elongate recess and the second elongate recess serve as guides for, respectively, the first inner pull-wire and the second inner pull-wire to align the first inner pull-wire and the second inner pull-wire with fastening points at the control lever, and wherein the bottom surface of the first elongate recess and the bottom surface of the second elongate recess form an angle greater than 0 to align the first inner pull-wire and the second inner pull-wire with the fastening points at the control lever.

* * * * *